(12) United States Patent
Strongin et al.

(10) Patent No.: US 6,555,528 B2
(45) Date of Patent: Apr. 29, 2003

(54) DERIVATIZED BIOTIN COMPOUNDS AND METHODS OF USE

(75) Inventors: Robert M. Strongin, Baton Rouge, LA (US); Marcelo C. Saraiva, San Antonio, TX (US); Grover L. Waldrop, Baton Rouge, LA (US); David R. Amspacher, Baton Rouge, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 0 days.

(21) Appl. No.: 09/828,359

(22) Filed: Apr. 6, 2001

(65) Prior Publication Data

US 2001/0016343 A1 Aug. 23, 2001

Related U.S. Application Data

(62) Division of application No. 09/321,039, filed on May 27, 1999, now Pat. No. 6,242,610.

(51) Int. Cl.$^7$ ...................... A61K 31/42; C07D 235/02; A61P 43/00
(52) U.S. Cl. .................. 514/80; 514/387; 548/113; 548/303.7
(58) Field of Search ............................. 548/113, 303.7; 514/387, 80

(56) References Cited

U.S. PATENT DOCUMENTS 6,242,610 B1    6/2001 Strongin et al. .......... 548/303.7

OTHER PUBLICATIONS

Amspacher, D. et al., "Studies on the Catalytic Mechanism of Biotin," Abstract, Steenbock Symposium (University of Wisconsin, Madison, May 28–31, 1998).
Amspacher, D. et al., "Synthesis of a Reaction Intermediate Analog of Biotin–Dependent Carboxylases via a Selective Derivatization of Biotin," manuscript submitted to Organic Letters (1999).
Amspacher, D. et al., "Synthesis and Characterization of a Slow–Binding Inhibitor of Biotin Carboxylase," pp. 131–138 in P. Frey et al. (eds.), Enzymatic Mechanisms (1999).
Amspacher, D. et al., "The Synthesis of a Slow–Binding Inhibitor of Biotin Carboxylase via a Selective Derivatization of Biotin," Poster presented at 216th American Chemical Society National Meeting (Boston, Aug. 23–27, 1998).
Amspacher, D. et al., "The Synthesis of a Slow–Binding Inhibitor of Biotin Carboxylase via a Selective Derivatization of Biotin," Newsletter and Abstracts, 216th American Chemical Society National Meeting (Boston, Aug. 23–27, 1998).
Berkessel, A. et al., "On the Structures of Some Adducts of Biotin with Electrophiles . . . ," Biorganic Chem., vol. 14, pp. 249–261 (1986).
Blanchard, C. et al., "Inhibition of Biotin Carboxylase by a Reaction Intermediate Analog: Implications for the Kinetic Mechanism" pp. 1–17 (unpublished manuscript, 1999).
Blanchard, C. et al., "Mutations at Four Active Site Residues of Biotin Carboxylase Abolish Substrate–Induced Synergism by Biotin," Biochemistry, vol. 38, pp. 3393–3400 (1999).
Guchhait, R. et al., J. Biol. Chem. vol. 249, pp. 6646–6656 (1974).
Han, Q. et al., "Synthesis of (+)–Biotin Derivatives as HIV–1 Protease Inhibitors," Bioorg. & Med. Chem., vol. 6, pp. 1371–1374 (1996).
Knappe, J. et al., Biochemishe Zeitschrift, vol. 335, pp. 168–176 (1961).
Tipton, P. et al., "Catalytic Mechanism of Biotin Carboxylase: Steady–State Kinetic Investigations," Biochemistry, vol. 27, pp. 4317–4325 (1988).
Product No. H–9040 Analytical Data Sheet, BACHEM Bioscience (1999?).

*Primary Examiner*—Joseph K. McKane
*Assistant Examiner*—Andrea D. Small
(74) *Attorney, Agent, or Firm*—John H. Runnels

(57) ABSTRACT

An efficient synthesis for the selective and efficient 1'-N derivatization of biotin is reported. The derivatized biotin acts as a stable analog of the carboxyphosphate intermediate in naturally-occurring biotin-mediated $CO_2$ transfer. The synthesis may readily be scaled up to perform large-scale, selective acylations of biotin. The stable analog of the intermediate can inhibit the activity of the biotin carboxylase enzymes such as acetyl CoA carboxylase, and HIV protease. The functionalization at the 1'-N of biotin results in the attachment of an electrophilic "handle" amenable to reaction with a wide variety of nucleophiles to generate a new family of biotin analogs.

15 Claims, 2 Drawing Sheets

DERIVATIZED BIOTIN COMPOUNDS AND METHODS OF USE

This is a divisional of application Ser. No. 09/321,039, filed May 27, 1999, now U.S. Pat. No. 6,242,610, issued Jun. 5, 2001.

The development of this invention was funded in part by the Government under cooperative grant number GM51261 awarded by the National Institutes of Health. The Government has certain rights in this invention.

This invention pertains to derivatized biotin compounds, and to methods of using those compounds.

Biotin (also known as vitamin H) is an essential growth factor found in all animals, plants, fungi, and bacteria. It is found, for example, bound to proteins or polypeptides in the liver, pancreas, kidney, milk, and in yeasts. Biotin is a cofactor for a group of enzymes that catalyze carboxylation reactions, transcarboxylation reactions, and decarboxylation reactions. The reactions catalyzed by biotin-dependent enzymes are involved in several essential metabolic pathways, including gluconeogenesis, fatty acid synthesis, and amino acid catabolism. All biotin-dependent carboxylases catalyze their respective reactions via the two step reaction shown below:

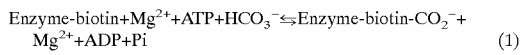

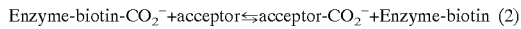

R. Guchhait et al., *J. Biol. Chem.* vol. 249, pp. 6646–6656 (1974) showed that in the first partial reaction shown above, biotin is carboxylated on the 1'-N. Since bicarbonate is the source of $CO_2$ for all biotin-dependent carboxylases, carboxylation of the 1'-N of biotin is accomplished by activating bicarbonate through phosphorylation with ATP to form a carboxyphosphate intermediate. The carboxyl group is then transferred from the carboxyphosphate intermediate to biotin to form carboxybiotin.

In the field of biotechnology, biotin has become an important reagent in methods to label, detect, and purify proteins and nucleic acids. These methods are based on the remarkable affinity between biotin and the proteins avidin and streptavidin. The dissociation constant of biotin from avidin or streptavidin is about $10^{-15}$M, one of the strongest known interactions between a protein and a ligand. While all parts of the biotin molecule contribute to this tight binding, hydrogen bonding donation by the ureido nitrogens is the major contributor.

Q. Han et al., "Synthesis of (+)-Biotin Derivatives as HIV-1 Protease Inhibitors," *Bioorg. & Med. Chem.*, vol. 6, pp. 1371–1374 (1996) reported the synthesis of several bis-N-alkylated biotin derivatives, and their activity against HIV-1 protease. All biotin derivatives reported in this paper were substituted on both urea nitrogens. There was no suggestion to selectively substitute biotin at one of the nitrogen atoms only, nor was there any suggestion of how such a selective synthesis might be performed.

Up to 25% diacylated biotin products have previously been reported following acylation of biotin methyl ester with (1) methylchloroformate or (2) trifluoroacetic anhydride. See (1) J. Knappe et al., *Biochemishe Zeitschrift*, vol. 335, pp. 168–176 (1961); and (2) A. Berkessel et al., *Bioorganic Chem.*, vol. 14, pp. 249–261 (1986); respectively.

P. Tipton et al., "Catalytic Mechanism of Biotin Carboxylase: Steady-State Kinetic Investigations," *Biochemistry*, vol. 27, pp. 4317–4325 (1988) reported that no biotin analog that had been tested had inhibited biotin carboxylase (at page 4322).

The ureido ring of biotin is of great importance in binding to avidin, and the 1'-N of that ring is directly involved in biotin's role as a carboxytransfer intermediate. However, there have been relatively few studies involving functionalization of the 1'-N of biotin. Most prior research on derivatizing biotin has involved acylation chemistry at the carboxylic acid terminus of the pendant alkyl chain.

We have discovered a method to functionalize biotin at the 1'-N, selectively and with high efficiency. The resulting 1'-N-substituted biotin has an electrophilic "handle" that is amenable to reaction with a wide variety of nucleophiles to generate a new family of biotin analogs. Such nucleophiles might include, for example, acetyl coenzyme A, benzyl alcohol, benzoic acid, aniline, or other nucleophiles known in the art.

This synthesis is more selective for functionalization at the 1'-N of biotin than have been any known prior syntheses. Compounds prepared from the 1'-N-substituted biotin are useful in inhibiting various enzymatic reactions, including the inhibition of HIV protease.

As initial examples, we have synthesized compounds 1 and 3 (see FIGS. 1 and 2). Compound 1 is formally derived from phosphonoacetic acid coupled to the 1'-N of biotin. The synthesis of Compound 3 was highly efficient and selective: a 98% yield with essentially 100% selectivity, in a synthesis conducted on the multi-gram scale. The synthesis of Compound 1 had an overall yield of 35%, and a 100% selectivity.

We have shown that compound 1 acts as a stable analog of the carboxyphosphate intermediate in naturally-occurring biotin-mediated $CO_2$ transfer. Compound 1 inhibits the activity of the biotin carboxylase component of the enzyme acetyl CoA carboxylase. This is the first reported biotin-derived inhibitor of biotin carboxylase.

The synthesis of Compound 3 may readily be scaled up to perform large-scale, selective acylations of biotin to form Compound 1 or other end products.

Materials and Methods

Figure 1:
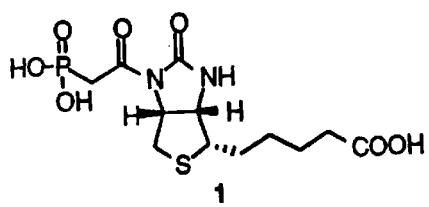
FIG. 1 depicts target compound 1.
Figure 2:
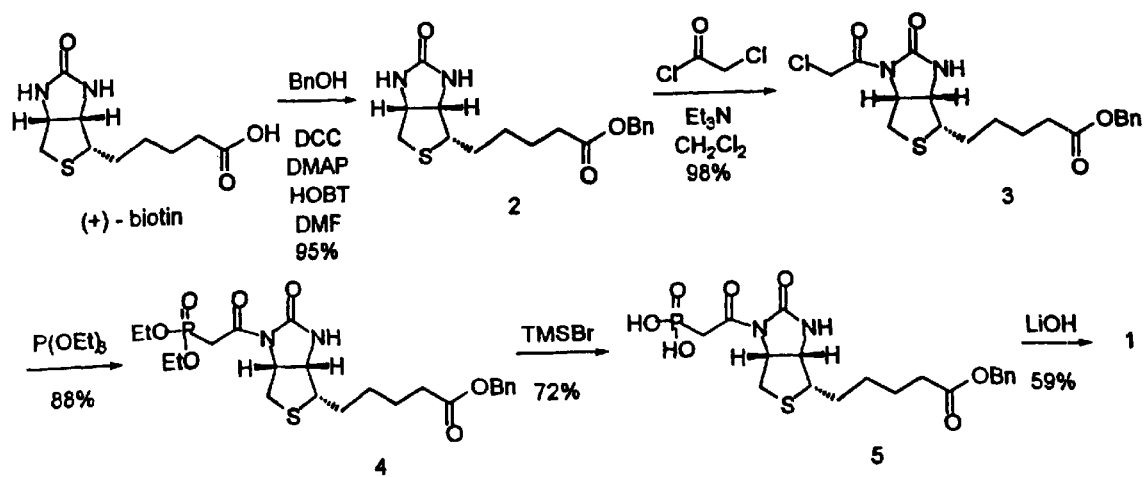
FIG. 2 depicts the overall synthetic scheme for the synthesis of compounds 1, 3, and various intermediates.

Metal-chelating, histidine-binding resin was purchased from Novagen. Pyruvate kinase was purchased from Boehringer Mannheim. All other reagents were purchased from Sigma or Aldrich. Unless otherwise noted, all nonaqueous reactions were carried out under a dry nitrogen atmosphere in flame-dried glassware. $CH_2Cl_2$ was distilled over $CaH_2$ immediately prior to use. DMF was purchased from Aldrich in sure/seal bottles and was used without further purification. Analytical thin-layer chromatography (TLC) was performed with general purpose 60-Å silica gel on glass (Aldrich). TLC plates were visualized with aqueous $KMnO_4$. Flash chromatography columns were prepared with Kieselgel 60-Å silica gel, 230–400 mesh (Merck). Proton ($^1$H), Carbon ($^{13}$C), and Phosphorus ($^{31}$P) N spectra were measured on a Bruker ARX300 300 MHz spectrometer. IR spectra were measured on a Perkin Elmer 1760X FT-IR spectrometer. Mass spectrometry was provided by the Washington University Mass Spectrometry Resource.

Phenylmethyl 5-(6,8-Diaza-oxo-3-thiabicyclo[3.3.0] oct-2-yl) Pentanoate (Compound 2)

The synthesis of compound 1 began by protecting (+)-biotin as the corresponding benzyl ester in 95% yield by stirring a DMF solution (60 ml) of biotin, (10.2 g, 42.6 mmol, 1 equiv), benzyl alcohol (5.6 g, 52 mmol, 1.2. equiv), DCC (46.2 ml of a 1 M solution in $CH_2Cl_2$, 46.2 mmol, 1.1 equi), DMAP (0.51 g, 4.2 mmol, 0.1 equiv), HOBT (0.64 g, 4.2 mmol, 0.1 equiv), at room temperature for 12 hours.

More particularly, (+)-Biotin (10.20 g, 42 mmol), DMAP (0.51 g, 4.2 mmol), HOBT (0.64 g, 4.2 mmol) and benzyl alcohol (5.64 g, 52 mmol) were added to 60 ml of DMF in a 500 ml, 3-neck flask. The mixture was stirred and heated until a homogenous solution was obtained. DCC (46.2 ml of a 1M solution in $CH_2Cl_2$) was added over 10 min, and the reaction mixture was stirred 12 hours at room temperature. The reaction mixture was filtered and the filtrate concentrated in vacuo. The resulting solid was dissolved in hot acetone (50° C.) and purified by flash chromatography with 10% MeOH/90% EtOAc to produce a white solid, compound 2 (13.3 g, 95% yield): m.p. 79° C.; $^1$H NMR (DMSO-$d_6$) δ7.36 (s, 5H), 6.43 (s, 1H), 6.36, (s, 1H), 5.08, (s, 2H), 4.29, (m, 1H), 4.13, (m,1H), 3.07, (m, 1H), 2.84–2.50, (m, 2H), 2.36, (t, J=7.2 Hz, 2H), 1.65–1.25, (m, 6H); $^{13}$C (DMSO-$d_6$) δ173.59, 163.56, 137.15, 129.30, 128.79, 66.18, 61.88, 60.03, 56.20, 34.15, 28.84, 25.37; IR (KBr) 3244, 2930, 1740, 1692, 1458, 1262, 1170, 737, 698; HRMS: found 335.1432 ($C_{17}H_{23}N_2O_3S$=335.1429 MH$^+$).

Phenylmethyl5-(6,8-diaza-6-(2-chloroacetyl)-7-oxo-3-thiabicyclo[3.3.0]oct-2-yl)pentanoate (Compound 3)

Chloride 3 was prepared in 98% yield by careful dropwise addition of $Et_3N$ (7.06 ml, 5.1 mmol, 3 equiv) and chloroacetylchloride (1.95 ml, 25 mmol, 1.5 equiv) in three portions to a solution of biotin benzyl ester (5.6 g, 17 mmol, 1 equiv) in $CH_2Cl_2$ at −78° C., followed by warming to room temperature and holding for 12 hours.

More particularly, (5.6 g, 17 mmol) of compound 2 and (7.06 ml, 51 mmol) $Et_3N$ were added to 40 ml of $CH_2Cl_2$. Chloroacetylchloride (1.95 ml, 25.2 mmol) was added in three portions. The mixture was stirred and brought to −78° C. and (0.65 ml, 8.4 mmol) of chloroacetylchloride was added. The mixture was stirred for 12 hours and allowed to warm to room temperature. The same series of steps was repeated 2 more times. The reaction mixture was filtered, and the filtrate was evaporated in vacuo to a thick oil, which was then dissolved in $CH_2Cl_2$ and purified by flash chromatography with 4% MeOH/48% hexane/48% EtOAc to afford a yellowish oil 3 (6.9 g, 98% yield); $^1$H NMR (DMSO-$d_6$) δ8.11, (s, 1H), 7.36 (s, 5H), 5.08, (s, 2H), 4.81, (m, 3H), 4.19, (m, 1H), 3.20, (m, 1H), 3.03–2.83, (m, 2H), 2.37, (t, J=7.2 Hz, 2H), 1.71–1.23, (m, 6H); $^{13}$C NMR (DMSO-$d_6$) δ173.56, 166.32, 156.64, 137.14, 129.14, 128.80, 66.20, 62.20, 58.84, 55.42, 44.89, 38.03, 34.10, 28.81, 25.24; IR (thin film) 3332, 3134, 2937, 1735, 1704, 1395, 1358, 1241, 792, 752, 699; HRMS: found 411. ($C_{19}H_{23}ClO_4N_2S$=411.1245 MH$^+$).

No diacylated product was observed. Up to 25% diacylated product has been reported upon acylation of biotin methyl ester with (1) methylchloroformate or (2) trifluoroacetic anhydride. See (1) J. Knappe et al., *Biochemishe Zeitschrift*, vol. 335, pp. 168–176 (1961); and (2) A. Berkessel et al., *Bioorganic Chem.*, vol. 14, pp. 249–261 (1986); respectively. In other experiments, we obtained up to 10% diacylation upon reaction of biotin methyl ester with chloroacetylchloride as evidenced by 1H NMR. Energy minimization computer studies (using Sybil™ software, version 6.1) showed that the benzyl moiety blocked the 3'-N more effectively than would a methyl group.

Other halogens could be substituted for the chlorine atom in Compound 3. To synthesize other halogen-substituted analogs of Compound 3, one could substitute other haloacetyl chlorides in the above synthesis for chloroacetyl chloride; e.g., $FCH_2COCl$, $BrCH_2COCl$, or $ICH_2COCl$. Substituting Br or I for Cl might make the substitution reactions faster. More generally, one could synthesize a phenylmethyl 5-(6,8-diaza-6-(2-X-acetyl)-7-oxo-3-thiabicyclo[3.3.0]oct-2-yl)pentanoate, wherein X is a h by reacting biotin with an acid halide also containing a primary, secondary, or tertiary halide in a solvent comprising a non-nucleophilic base. The non-nucleophilic base acts as an "acid sponge" to absorb acids (such as HCl) generated in the reaction mixture, without itself participating in a nucleophilic attack. Examples of such non-nucleophilic bases include, e.g., triethyl amine and pyridine.

A 1'-N-substituted biotin compound may be synthesized by reacting a phenylmethyl 5-(6,8-diaza-6-(2-X-acetyl)-7-oxo-3-thiabicyclo[3.3.0]oct-2-yl)pentanoate with a nucleophile, under reaction conditions favorable to nucleophilic substitution, wherein X is a halogen atom.

Phenylmethyl5-(6,8-diaza-6-(2-diethoxyphosphono) acetyl)-7-oxo-3-thiabicyclo[3.3.0]oct-2-yl) pentanoate (Compound 4)

Compound 3 (6.9 g, 17 mmol, 1 equiv) underwent an Arbuzov reaction at 100° C. in $P(OEt)_3$ solvent (20 ml) to afford the phosphonate ester 4 in 89% yield. The structure of 4 was confirmed by x-ray crystallography.

More particularly, (6.88 g, 17 mmol) of compound 3 and triethyl phosphite (20 ml) were added to a 100 ml, 3-neck flask and heated to 100° C. with stirring for 3 hours. The excess triethyl phosphite was evaporated in vacuo. The resulting viscous oil was dissolved in $CH_2Cl_2$ and purified by flash chromatography using a gradient of 4% MeOH/48% hexane/48% EtOAc to 10% MeOH 90% EtOAc, to give a yellowish oil, compound 4 (7.6 g, 89%). Crystals were obtained by evaporating a solution of 4 in EtOAc; $^1$H NMR (CDCl$_3$) δ7.28, (s, 5H), 5.04, (s, 2H), 4.85, (t, 1H), 4.09, (q,J=6.9 Hz, 4H), 3.78, (m, 1H), 3.09, (m, 1H), 2.94, (m, 1H), 2.29, (t, J=7.2 Hz, 2H), 1.74–1.36, (m, 6H), 1.28, (t,J=6.9 Hz, 6H); $^{31}$P (DMSO-$d_6$) δ21.3, (s); $^{13}$C NMR (DMSO-$d_6$d 173.56, 165.02, 157.51, 156.60, 137.14, 129.30, 128.79, 66.20, 62.57, 62.11, 60.62, 57.68, 55.46, 38.29, 34.64, 34.108, 32.92, 28.81, 28.58, 25.24; IR (thin film) 3328, 3262, 2981, 2935, 2867, 1737, 1678, 1396, 1351, 1251, 1025, 753, 699; HRMS: found 513.1828 ($C_{23}H_{33}N_2O_7PS$=513.1824 MH$^+$). Crystal data for 4: $C_{23}H_{33}N_2O_7PS$,monoclinic space group P$2_1$, a=10.546(1), b=12.550(1), c=10.674(1) Å, β=112.15(1)°, V=1308.4(5) Å$^3$, Z=2, colorless, T=299° K., R=0.096, GOF=4.753. Displacement parameters of the benzyl ester and phosphonate groups were large; low temperature data collection is also planned Phenylmethyl 5-(6,8-Diaza-7-oxo-6-(2-phosphonoacetyl)-3-thiabicyclo[3.3.0] Oct-2-yl) Pentanoate (Compound 5)

Phosphonate ester hydrolysis of 4 (4.75 g, 9.3 mmol, 1 equiv) promoted by TMSBr (3.7 ml, 28 mmol, 3 equiv) afforded 3.0 g (72% yield) of phosphonic acid 5.

More particularly, to a flask with $CH_2Cl_2$ (40 ml), (4.75 g, 9.26 mmol) of compound 4 were added. TMSBr (3.67 ml, 28 mmol) was added and the mixture was stirred for 2 hours at room temperature. The reaction was quenched with 5 ml of distilled water and concentrated in vacuo. The solid was recrystallized in water/methanol (9:1) to afford a white solid, compound 5. (3.03 g, yield 72%); m.p. 184° C.; $^1$H NMR (DMSO-d$_6$) δ7.96, (s, 1H), 7.36, (s, 5H), 5.1, (s, 2H), 4.77 (t, 1H), 4.1, (m, 1H), 3.5, (m, 2H), 3.2 (m, 2H), 3.07–2.80, (m, 2H), 2.37, (t, J=7.2 Hz, 2H (DMSO-d$_6$) δ15.5, (s); $^{13}$C NMR (DMSO-d$_6$) δ173.57, 166.40, 157.48, 156.61, 129.31, 128.81. 66,20, 62.10, 57.64, 55.40, 38.47, 35.44, 34.11, 28.82, 28.60, 25.25; IR (KBr) 3434, 2935, 2856, 1737, 1682, 1399, 1356, 1233, 1184, 1149, 753, 698; HRMS: found 457.1194 ($C_{19}H_{25}N_2O_7PS$=457.1198 MH$^+$).

5-(6,8-Diaza-7-oxo-6-(2-phosphonoacetyl)-3-thiabicyclo[3.3.0] Oct-2-yl) pentanoic acid
(Compound 1)

Subsequent saponification of 5 (0.51 g, 1.1 mmol, 1 equiv) with LiOH (0.21 g, 4.9 mmol, 4.5 equiv) afforded the water soluble target 1 (59% yield).

More particularly, (0.21 g, 4.9 mmol) of LiOH was added to a solution (0.506 g, 0.000225 moles) of compound 5 in 40 ml of water. The reaction mixture was filtered, and the filtrate was concentrated in vacuo and recrystallized in water/acetone (9:1) to afford a white solid, compound 1. (0.209 g, yield 59%); 1H NMR (D$_2$O) δ4.50, (m, 1H), 4.34, (m, 1H), 3.25, (m, 1H), 2.92–2.64, (m, 2H), 2.43–2.36, (m, 2H), 2.06, (t, J=7.2 Hz, 2H). 1.69–1.25, (m, 6H); $^{31}$P (D$_2$O) δ14.9 (s); $^{13}$C NMR (D$_2$O) δ157.49, 62.33, 60.59, 55.69, 41.38, 40.05, 39.86, 37.65, 28.59, 28.00, 25.00; IR (KBr) 3344, 3196, 2922, 2851, 1702, 1661, 1567, 1431, 1138, 1074, 869; MS: found 394.4 ($C_{12}H_{17}LiN_2NaO_7PS$=394.0552 MH$^+$).

Purification and Assay of Biotin Carboxylase Inhibition

Compound 1 was used in enzyme inhibition studies to demonstrate that it is a reaction intermediate analog of biotin-dependent carboxylases. As a prototype example, we examined the effect of Compound 1 on the activity of biotin carboxylase from *Escherichia coli*. Biotin carboxylase is one component of *E. coli* acetyl CoA carboxylase. It catalyzes the first partial reaction shown above as reaction (1). We chose *E. coli* biotin carboxylase as a model for biotin-dependent carboxylases generally because it was readily available—its gene has been cloned and overexpressed. See S. Li et al., *J. Biol. Chem.*, vol. 267, 855–863 (1992); and H. Kondo et al., *Proc. Natl. Acad. Sci. USA*, vol. 88, pp. 9730–9733 (1991). In addition, the crystal structure of biotin carboxylase has been determined, and it is the first and currently only three-dimensional model of a biotin-dependent carboxylase available.

Acetyl CoA carboxylase catalyzes the biotin-dependent carboxylation of acetyl CoA to form malonyl CoA in the first step of fatty acid biosynthesis. The *E. coli* acetyl CoA carboxylase has three components: (1) biotin carboxylase, which catalyzes the ATP-dependent carboxylation of biotin (step 1 in the reaction shown above), (2) the biotin carboxyl carrier protein, which contains the biotin moiety cofactor in which biotin is covalently linked to a lysine residue via an amide linkage to the valeric acid carboxyl, and (3) carboxyl transferase, which catalyzes the transfer of the carboxyl group from carboxybiotin to acetyl CoA. Acetyl CoA carboxylase in humans is a target for antihyperlipidemic drugs. Acetyl CoA carboxylase in plants is a target for several herbicides.

Biotin carboxylase was purified from a strain of *E. coli* that overexpresses the gene coding for the enzyme, strain BL21(DE3)pLysS, obtained from Novagen (Madison, Wis.). Purification was performed with a histidine-tag attached to the amino terminus of a mutant form of the enzyme and nickel affinity chromatography as described in C. Blanchard et al., "Mutations at Four Active Site Residues of Biotin Carboxylase Abolish Substrate-Induced Synergism by Biotin," *Biochemistry*, vol. 38, pp. 3393–3400 (1999).

The activity of biotin carboxylase was measured spectrophotometrically by following the production of ADP. The amount of ADP was determined using pyruvate kinase and lactate dehydrogenase, and the oxidation of NADH was followed at 340 nm. Each measurement was carried out in a volume of 0.5 ml in 1 cm path length quartz cuvettes. The reaction mixture contained 10 units of pyruvate kinase, 18 units of lactate dehydrogenase, 0.5 mM phosphoenolpyruvate, 0.2 mM NADH, 8 mM MgCl$_2$ and 100 mM HEPES at pH 8.0. For inhibition studies compound 1 was dissolved in water, and the pH adjusted to 8 with HCl. The concentration of compound 1 was assayed by phosphorus analysis using the method of B. Ames et al., *J. Biol. Chem.*, vol. 235, pp. 769–775 (1960).

Figure 3:
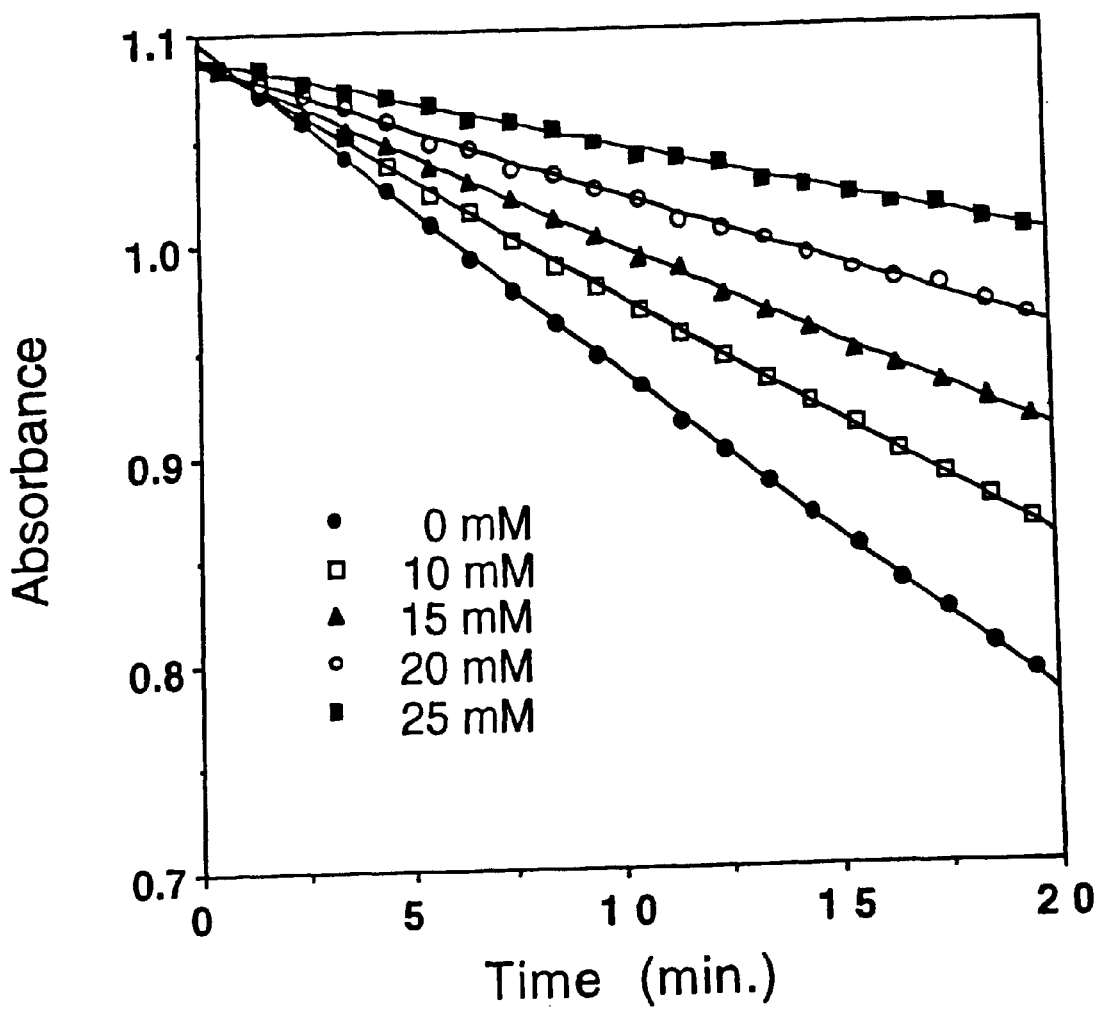
FIG. 3 depicts the activity of a biotin carboxylase in the absence of compound 1, and in the presence of increasing concentrations of compound 1.

We found that compound 1 inhibited the activity of biotin carboxylase significantly. FIG. 3 depicts the activity of biotin carboxylase in the absence of compound 1, and in the presence of increasing concentrations of compound 1. The substrate concentrations were in all cases held constant at 9 mM bicarbonate, 0.1 mM ATP, and 100 mM biotin.

The activity of biotin carboxylase decreased as the concentration of compound 1 increased. Preliminary characterization gave an inhibition constant of about 8 mM. While this value represents a modest degree of inhibition compared to the Km for biotin in biotin carboxylase (134 mM), recall that this inhibition was achieved simply by positioning a phosphonoacetyl moiety on the 1'-N of biotin. The addition of the phosphonoacetyl moiety increased the affinity of the compound for biotin carboxylase substantially. By contrast, P. Tipton et al., "Catalytic Mechanism of Biotin Carboxylase: Steady-State Kinetic Investigations," *Biochemistry*, vol. 27, pp. 4317–4325 (1988) reported that no biotin analog that had been tested had inhibited biotin carboxylase (at page 4322).

Compound 3 is an electrophilic coupling template that is useful not only in synthesizing Compound 1, but that is useful as an intermediate in synthesizing numerous other 1'-N substituted biotin compounds, compounds that will have uses as biotin agonists, antagonists, and biotin carboxylase inhibitors. The acyl halide "handle" on Compound 3 is a versatile tool allowing for ready reaction with a wide variety of nucleophiles. Currently we are preparing and testing a variety of congeners of 1 as inhibitors of biotin carboxylase, for example, Compound 1+AMP, Compound 1+ADP, and Compound 1+ATP. These compounds could serve as leads for novel antihyperlipidemic drugs and highly specific biodegradable herbicides, based on biotin carboxylase's role in fatty acid biosynthesis. A different congener may (or may not) be a better analog of the transition state, and thus could show better inhibition of the enzyme. For example, the compounds (including Compounds 1 and 3) will be used to inhibit proteases such as HIV protease.

For example, experiments are currently underway to confirm the effectiveness of Compounds 1 and 3 as inhibitors of HIV protease. Varying concentrations of these Compounds will be tested (starting at 8 mM, and increasing or decreasing by powers of 2) in a standard HIV protease inhibition assay to characterize the Compounds' effects on the enzyme. In particular, we will use the HIV protease activity assay of BACHEM Bioscience (King of Prussia, Pa.) based on recombinant HIV protease 1, with acetyl pepstatin as an inhibitor for control studies, in accordance with the manufacturer's recommendations. See Product No. H-9040 Analytical Data Sheet, BACHEM Bioscience (1999?).

A rigorous characterization of the inhibition of biotin carboxylase by 1 and its derivatives is also in progress in our laboratories. Preliminary results of these enzymology studies may be found in C. Blanchard et al., "Inhibition of Biotin Carboxylase by a Reaction Intermediate Analog: Implications for the Kinetic Mechanism" (unpublished manuscript, 1999). The analog showed competitive inhibition versus ATP with a slope inhibition constant of 8 mM. Noncompetitive inhibition was found for the analog versus biotin. Phosphonoacetate exhibited competitve inhibition with respect to ATP and noncompetitve inhibition versus bicarbonate. Multiple inhibition studies indicated that the binding of the reaction intermediate analog and ADP or AMP to biotin carboxylase was mutually exclusive. Biotin was found to be a noncompetitive substrate inhibitor of biotin carboxylase. These data were interpreted as biotin carboxylase having an ordered addition of substrates, with ATP binding first, followed by bicarbonate, with biotin binding last.

When used as an HIV protease inhibitor in vivo, a compound in accordance with the present invention may be administered to a patient by any suitable means, including oral, intravenous, parenteral, subcutaneous, intrapulmonary, and intranasal administration. Parenteral infusions include intramuscular, intravenous, intraarterial, or intraperitoneal administration. The compound may also be administered transdermally, for example in the form of a slow-release subcutaneous implant, or orally in the form of capsules, powders, or granules. It may also be administered by inhalation.

Pharmaceutically acceptable carrier preparations for parenteral administration include sterile, aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. The active therapeutic ingredient may be mixed with excipients that are pharmaceutically acceptable and are compatible with the active ingredient. Suitable excipients include water, saline, dextrose, glycerol and ethanol, or combinations thereof. Intravenous vehicles include fluid and nutrient replenishers, electrolyte replenishers, such as those based on Ringer's dextrose, and the like. Preservatives and other additives may also be present such as, for example, antimicrobials, anti-oxidants, chelating agents, inert gases, and the like.

The form may vary depending upon the route of administration. For example, compositions for injection may be provided in the form of an ampule, each containing a unit dose amount, or in the form of a container containing multiple doses.

The compound maybe formulated into therapeutic compositions as pharmaceutically acceptable salts. These salts include acid addition salts formed with inorganic acids, for example hydrochloric or phosphoric acid, or organic acids such as acetic, oxalic, or tartaric acid, and the like. Salts also include those formed from inorganic bases such as, for example, sodium, potassium, ammonium, calcium or ferric hydroxides, and organic bases such as isopropylamine, trimethylamine, histidine, procaine and the like.

Controlled delivery may be achieved by admixing the active ingredient with appropriate macromolecules, for example, polyesters, polyamino acids, polyvinyl pyrrolidone, ethylenevinylacetate, methylcellulose, carboxymethylcellulose, prolamine sulfate, or lactide/glycolide copolymers. The rate of release of the active compound may be controlled by altering the concentration of the macromolecule.

Another method for controlling the duration of action comprises incorporating the active compound into particles of a polymeric substance such as a polyester, peptide, hydrogel, polylactide/glycolide copolymer, or ethyleneviny-lacetate copolymers. Alternatively, an active compound may be encapsulated in microcapsules prepared, for example, by coacervation techniques or by interfacial polymerization, for example, by the use of hydroxymethylcellulose or gelatin-microcapsules or poly(methylmethacrylate) microcapsules, respectively, or in a colloid drug delivery system. Colloidal dispersion systems include macromolecule complexes, nanocapsules, microspheres, beads, and lipid-based systems including oil-in-water emulsions, micelles, mixed micelles, and liposomes.

A problem with existing uses of biotin in biotin/avidin or biotin/streptavidin systems is that the strong affinity of these pairs makes it difficult to isolate a protein or nucleic acid bound to one member of the pair. Modification of the 1'-N of biotin may lessen the binding avidity of biotin to avidin and streptavidin, thereby making it easier to isolate the protein or nucleic acid.

The complete disclosures of all references cited in this specification are hereby incorporated by reference. Also incorporated by reference are the following publications of the inventors' own work, which are not prior art to this application: D. Amspacher et al., "Synthesis of a Reaction Intermediate Analog of Biotin-Dependent Carboxylases via a Selective Derivatization of Biotin," manuscript submitted to *Organic Letters* (1999); D. Amspacher et al., "Studies on the Catalytic Mechanism of Biotin," Abstract, Steenbock Symposium (University of Wisconsin, Madison, May 28–31, 1998); D. Amspacher et al., "Synthesis and Characterization of a Slow-Binding Inhibitor of Biotin Carboxylase," pp. 131–138 in P. Frey et al. (Eds.), *Enzymatic Mechanisms* (1999); D. Amspacher et al., "The Synthesis of a Slow-Binding Inhibitor of Biotin Carboxylase via a Selective Derivatization of Biotin," Poster presented at 216th American Chemical Society National Meeting (Boston, Aug. 23–27, 1998); D. Amspacher et al., "The Synthesis of a Slow-Binding Inhibitor of Biotin Carboxylase via a Selective Derivatization of biotin," *Newsletter and Abstracts,* 216th American Chemical Society National Meeting (Boston, Aug. 23–27, 1998).

In the event of an otherwise irreconcilable conflict, however, the present specification shall control.

We claim:

1. A method for synthesizing a 1'-N-substituted biotin compound, said method comprising reacting phenylmethyl 5-(6,8-diaza-6-(2-X-acetyl)-7-oxo-3-thiabicyclo[3.3.0]oct-2-yl)pentanoate with a nucleophile, under reaction conditions favorable to nucleophilic substitution, wherein X is a halogen atom.

2. A method as recited in claim 1, wherein X is fluorine.

3. A method as recited in claim wherein 1, wherein X is chlorine.

4. A method as recited in claim 1, wherein X is bromine.

5. A method as recited in claim 1, wherein X is iodine.

6. A 1'-N substituted biotin compound produced by the method of claim 1.

7. A 1'-N substituted biotin compound produced by the method of claim 2.

8. A 1'-N substituted biotin compound produced by the method of claim 3.

9. A 1'-N substituted biotin compound produced by the method of claim 4.

10. A 1'-N substituted biotin compound produced by the method of claim 5.

11. A method for inhibiting the activity of HIV protease, comprising reacting the protease with an amount of a compound as recited in claim 6 sufficient to reduce the activity of the protease to a statistically significant degree.

12. A method for inhibiting the activity of HIV protease, comprising reacting the protease with an amount of a compound as recited in claim 7 sufficient to reduce the activity of the protease to a statistically significant degree.

13. A method for inhibiting the activity of HIV protease, comprising reacting the protease with an amount of a compound as recited in claim 8 sufficient to reduce the activity of the protease to a statistically significant degree.

14. A method for inhibiting the activity of HIV protease, comprising reacting the protease with an amount of a compound as recited in claim 9 sufficient to reduce the activity of the protease to a statistically significant degree.

15. A method for inhibiting the activity of HIV protease, comprising reacting the protease with an amount of a compound as recited in claim 10 sufficient to reduce the activity of the protease to a statistically significant degree.

\* \* \* \* \*